(12) United States Patent
Old et al.

(10) Patent No.: US 7,998,998 B2
(45) Date of Patent: *Aug. 16, 2011

(54) THERAPEUTIC SUBSTITUTED LACTAMS

(75) Inventors: David W. Old, Irvine, CA (US); Vinh X. Ngo, Huntington Beach, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/739,676

(22) PCT Filed: Oct. 16, 2008

(86) PCT No.: PCT/US2008/080063
§ 371 (c)(1),
(2), (4) Date: Jul. 7, 2010

(87) PCT Pub. No.: WO2009/055289
PCT Pub. Date: Apr. 30, 2009

(65) Prior Publication Data
US 2010/0292293 A1 Nov. 18, 2010

Related U.S. Application Data

(60) Provisional application No. 60/981,918, filed on Oct. 23, 2007, provisional application No. 60/984,838, filed on Nov. 2, 2007.

(51) Int. Cl.
C07D 409/02 (2006.01)
A61K 31/38 (2006.01)
A61K 31/395 (2006.01)

(52) U.S. Cl. ........................................ 514/422; 548/527

(58) Field of Classification Search ................... 514/422; 548/527
See application file for complete search history.

(56) References Cited

U.S. PATENT DOCUMENTS
2005/0009840 A1  1/2005 Cui et al.

FOREIGN PATENT DOCUMENTS
EP           0483667       5/1992
WO      WO 03/008377       1/2003
WO      WO 2005/108360    11/2005

OTHER PUBLICATIONS

"Glaucoma." URL: http://www.webmd.com/eye-health/glaucoma-eyes Nov. 1, 2010.*
U.S. Appl. No. 11/836,655, filed Aug. 9, 2007, David W. Old.
U.S. Appl. No. 11/553,143, filed Oct. 26, 2006, Yariv Donde.
Prodrugs and Drug Delivery Systems, which is a chapter in Richard B. Silverman, Organic Chemistry of Drug Design and Drug Action, 2d Ed., Elsevier Academic Press: Amsterdam, 2004, pp. 496-557.

* cited by examiner

*Primary Examiner* — Rebecca Anderson
*Assistant Examiner* — Samantha Shterengarts
(74) *Attorney, Agent, or Firm* — Doina G. Ene; John E Wurst; Kevin J. Forrestal

(57) ABSTRACT

Disclosed herein are compounds having a formula: (I) Compositions, methods, and medicaments related thereto are also disclosed.

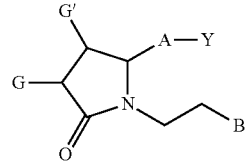

19 Claims, No Drawings

THERAPEUTIC SUBSTITUTED LACTAMS

CROSS-REFERENCE

This is a national stage application under 35 U.S.C. §371 of PCT patent application PCT/US08/80063, filed on Oct. 16, 2008, which claims the benefit of U.S. Provisional Application Ser. No. 60/981,918, filed Oct. 23, 2007 and U.S. Application Ser. No. 60/984,838, filed Nov. 2, 2007, each of which is hereby incorporated by reference in its entirety.

DESCRIPTION OF THE INVENTION

Disclosed herein are compounds having a formula:

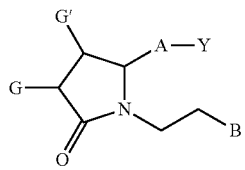

wherein Y has from 0 to 14 carbon atoms and is: an organic acid functional group, or an amide or ester thereof; hydroxymethyl or an ether thereof; or a tetrazolyl functional group;

A is —$(CH_2)_6$—, cis —$CH_2CH=CH—(CH_2)_3$—, or —$CH_2C≡C—(CH_2)_3$—, wherein 1 or 2 carbon atoms may be replaced by S or O; or A is —$(CH_2)_m$—Ar—$(CH_2)_o$— wherein Ar is interarylene, the sum of m and o is 1, 2, 3, or 4, and wherein 1 —$CH_2$— may be replaced by S or O, and 1 —$CH_2$—$CH_2$— may be replaced by —CH=CH— or —C≡C—;

G and G' are independently —H, —OH, —O-alkyl having from 1 to 6 carbon atoms, halo, $C_{1-6}$ alkyl, —$CF_3$, —CN, or =O; and B is aryl.

These compounds are useful for reducing intraocular pressure. Reduction of intraocular pressure has been shown to delay or prevent the onset of primary open angle glaucoma, and to delay or prevent further vision loss in patients with primary open angle glaucoma. Thus, these compounds are also useful for treating glaucoma. Different types of suitable dosage forms and medicaments are well known in the art, and can be readily adapted for delivery of the compounds disclosed herein. For example, the compound could be dissolved or suspended in an aqueous solution or emulsion that is buffered to an appropriate pH, and administered topically to an eye of a mammal.

For the purposes of this disclosure, "treat," "treating," or "treatment" refer to the use of a compound, composition, therapeutically active agent, or drug in the diagnosis, cure, mitigation, treatment, or prevention of disease or other undesirable condition.

Stable means that a compound is sufficiently stable to be stored in a bottle at room temperature under a normal atmosphere for at least 12 hours, or stable enough to be useful for any purpose disclosed herein.

Unless otherwise indicated, reference to a compound should be construed broadly to include pharmaceutically acceptable salts, prodrugs, tautomers, alternate solid forms, non-covalent complexes, and combinations thereof, of a chemical entity of a depicted structure or chemical name.

A pharmaceutically acceptable salt is any salt of the parent compound that is suitable for administration to an animal or human. A pharmaceutically acceptable salt also refers to any salt which may form in vivo as a result of administration of an acid, another salt, or a prodrug which is converted into an acid or salt. A salt comprises one or more ionic forms of the compound, such as a conjugate acid or base, associated with one or more corresponding counter-ions. Salts can form from or incorporate one or more deprotonated acidic groups (e.g. carboxylic acids), one or more protonated basic groups (e.g. amines), or both (e.g. zwitterions).

A prodrug is a compound which is converted to a therapeutically active compound after administration. For example, conversion may occur by hydrolysis of an ester group or some other biologically labile group. Prodrug preparation is well known in the art. For example, "Prodrugs and Drug Delivery Systems," which is a chapter in Richard B. Silverman, *Organic Chemistry of Drug Design and Drug Action*, 2d Ed., Elsevier Academic Press: Amsterdam, 2004, pp. 496-557, provides further detail on the subject. In particular, alkyl esters having such as methyl, ethyl, isopropyl, and the like are contemplated. Also contemplated are prodrugs containing a polar group such as hydroxyl or morpholine. Examples of such prodrugs include compounds containing the moieties —$CO_2(CH_2)_2OH$,

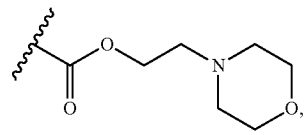

and the like.

Tautomers are isomers that are in rapid equilibrium with one another. For example, tautomers may be related by transfer of a proton, hydrogen atom, or hydride ion.

Unless stereochemistry is explicitly and unambiguously depicted, a structure is intended to include every possible stereoisomer, both pure or in any possible mixture.

Alternate solid forms are different solid forms than those that may result from practicing the procedures described herein. For example, alternate solid forms may be polymorphs, different kinds of amorphous solid forms, glasses, and the like.

Non-covalent complexes are complexes that may form between the compound and one or more additional chemical species that do not involve a covalent bonding interaction between the compound and the additional chemical species. They may or may not have a specific ratio between the compound and the additional chemical species. Examples might include solvates, hydrates, charge transfer complexes, and the like.

Y is an organic acid functional group, or an amide or ester thereof; or Y is hydroxymethyl or an ether thereof; or Y is a tetrazolyl functional group. For the purposes of this disclosure, Y is limited to from 0 to 14 carbon atoms, from 0 to 5 oxygen atoms, from 0 to 2 nitrogen atoms, from 0 to 2 sulfur atoms, and from 0 to 1 phosphorous, and any necessary hydrogen atoms.

An organic acid functional group is an acidic functional group on an organic molecule. While not intending to be limiting, organic acid functional groups may comprise an oxide of carbon, sulfur, or phosphorous. Thus, while not intending to limit the scope of the invention in any way, in certain compounds Y is a carboxylic acid, sulfonic acid, or phosphonic acid functional group.

Esters and amides of organic functional groups are carbonyl groups directly attached to a nitrogen or oxygen atom. Thus, esters of amides of carboxylic acids, sulfonic acid, and

| Acids | Esters | Amides |
|---|---|---|
| carboxylic acid | carboxylic acid ester | carboxylic acid amide |
| sulfonic acid | sulfonic acid ester | sulfonic acid amide |
| phosphonic acid | phosphonic acid ester | phosphonic acid amide |

An amide may also have an —$SO_2$— moiety. For example the amide —$CONHSO_2R^3$, wherein $R^3$ is a hydrocarbyl of from 1 to 14 carbon atoms, is contemplated. R, $R^1$, $R^2$, and $R^3$ are hydrocarbyl subject to the constraint that Y may not have more than 14 carbon atoms.

Hydrocarbyl is a moiety consisting of carbon and hydrogen, including, but not limited to:

a. alkyl, which is hydrocarbyl that contains no double or triple bonds, such as:

linear alkyl, e.g. methyl, ethyl, n-propyl, n-butyl, n-pentyl, n-hexyl, etc., branched alkyl, e.g. iso-propyl, t-butyl and other branched butyl isomers, branched pentyl isomers, etc., cycloalkyl, e.g. cyclopropyl, cyclobutyl, cyclopentyl, cyclohexyl, etc., combinations of linear, branched, and/or cycloalkyl;

b. alkenyl, which is hydrocarbyl having 1 or more double bonds, including linear, branched, or cycloalkenyl c. alkynyl, which is hydrocarbyl having 1 or more triple bonds, including linear, branched, or cycloalkynyl;

d. combinations of alkyl, alkenyl, and/or akynyl $C_{1-6}$ hydrocarbyl is hydrocarbyl having 1, 2, 3, 4, 5, or 6 carbon atoms.

$C_{1-6}$ alkyl is alkyl having 1, 2, 3, 4, 5, or 6, carbon atoms such as methyl, ethyl, propyl isomers, butyl isomers, pentyl isomer, and hexyl isomers, etc.

Hydroxyalkyl is alkyl-OH, such as hydroxymethyl, hydroxyethyl, etc. C1-6 hydroxyalkyl is hydroxyalkyl having 1, 2, 3, 4, 5, or 6, carbon atoms.

An ether of hydroxymethyl is —$CH_2OR$.

An unsubstituted tetrazolyl functional group has two tautomeric forms, which can rapidly interconvert in aqueous or biological media, and are thus equivalent to one another. These tautomers are shown below.

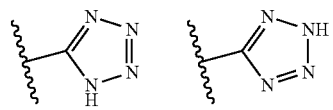

Additionally, if $R^2$ is $C_1$-$C_6$ alkyl, phenyl, or biphenyl, other isomeric forms of the tetrazolyl functional group such as the one shown below are also possible, unsubstituted and hydrocarbyl substituted tetrazolyl up to $C_{14}$ are considered to be within the scope of the term "tetrazolyl."

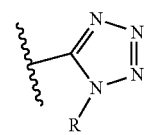

In one embodiment, Y is —$CO_2R^4$, —$CONR^5R^6$, —$CON(CH_2CH_2OH)_2$, —$CONH(CH_2CH_2OH)$, —$CH_2OH$, —$P(O)(OH)_2$, —$CONHSO_2R^4$, —$SO_2NR^5R^6$,

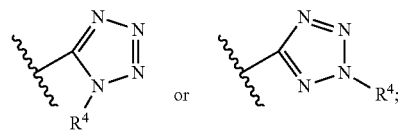

wherein $R^4$, $R^5$ and $R^6$ are independently H, $C_1$-$C_6$ alkyl, $C_{1-6}$ hydroxyalkyl, unsubstituted phenyl, or unsubstituted biphenyl, provided that Y has no more than 14 carbon atoms.

A is —$(CH_2)_6$—, cis —$CH_2CH=CH—(CH_2)_3$—, or —$CH_2C\equiv C—(CH_2)_3$—, wherein 1 or 2 carbon atoms may be replaced by S or O; or A is —$(CH_2)_m$—Ar—$(CH_2)_o$— wherein Ar is interarylene, the sum of m and o is 1, 2, 3, or 4, and wherein 1 —$CH_2$— may be replaced by S or O, and 1 —$CH_2$—$CH_2$— may be replaced by —$CH=CH$— or —$C\equiv C$—$(CH_2)_3$—.

Thus, A may be —$(CH_2)_6$—, cis —$CH_2CH=CH—(CH_2)_3$—, or —$CH_2C\equiv C—(CH_2)_3$—.

Alternatively, A may be a group which is related to one of these three moieties in that any carbon is replaced with S or O. For example, A may be a moiety where S replaces one or two carbon atoms such as one of the following or the like.

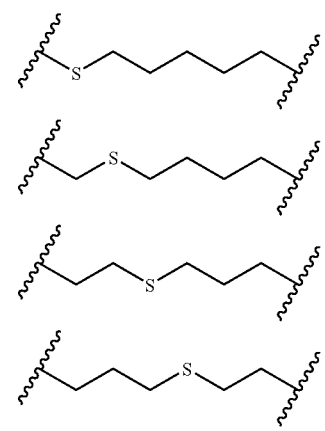

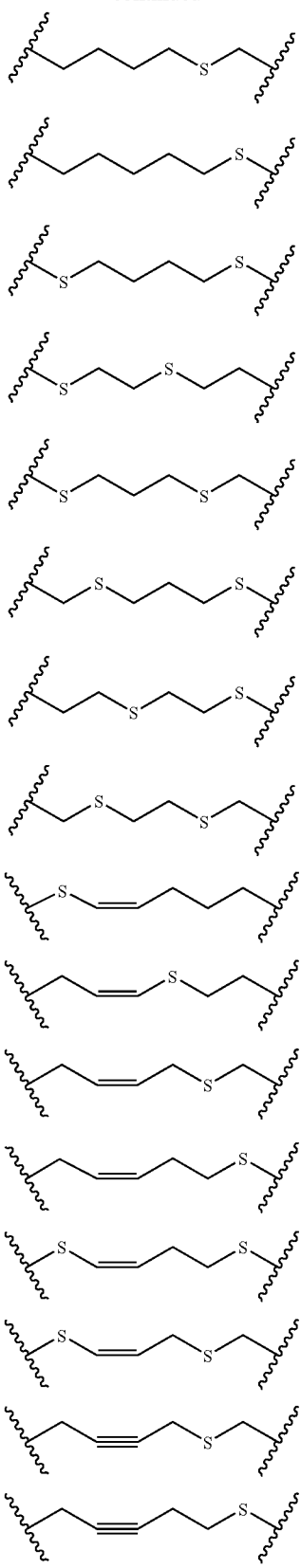
Alternatively, A may be a moiety where 0 replaces one or two carbon atoms such as one of the following or the like.
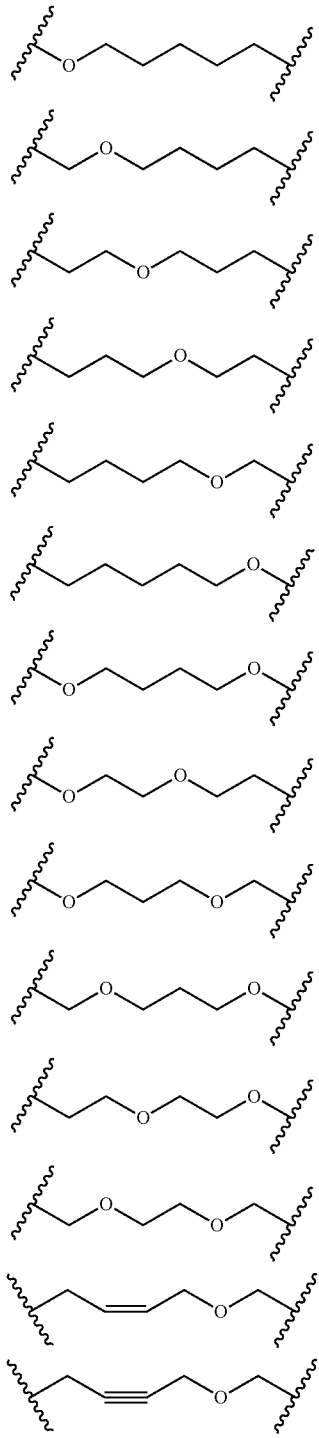
Alternatively, A may have an O replacing one carbon atom and an S replacing another carbon atom, such as one of the following or the like.
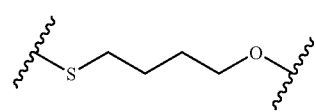

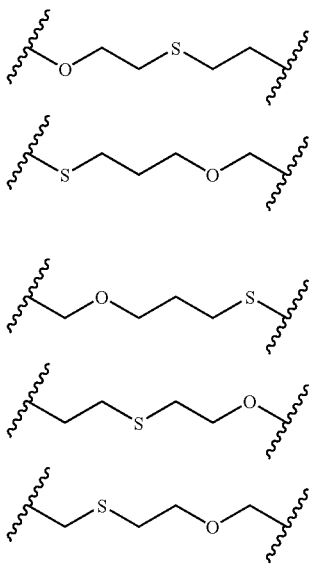

Alternatively, in certain embodiments A is —(CH$_2$)$_m$—Ar—(CH$_2$)$_o$— wherein Ar is interarylene or, the sum of m and o is 1, 2, 3, or 4, and wherein 1 —CH$_2$— may be replaced by S or O, and 1 —CH$_2$—CH$_2$— may be replaced by —CH=CH— or —C≡C—. In other words, in one embodiment A comprises:
1) a) 1, 2, 3, or 4 —CH$_2$— moieties, or
   b) 0, 1 or 2 —CH$_2$— moieties and —CH=CH— or —C≡C—; and
2) Ar;
e.g. —CH$_2$—Ar—, —(CH$_2$)$_2$—Ar—, —CH=CH—Ar—, —C≡C—Ar—, —CH$_2$—Ar—CH$_2$—, —CH$_2$Ar—(CH$_2$)$_2$—, —CH$_2$Ar—CH=CH—, —CH$_2$Ar—C≡C—, —(CH$_2$)$_2$—Ar—(CH$_2$)$_2$—, and the like;

in another embodiment A comprises:
1) a) O; and 0, 1, 2, or 3 —CH$_2$— moieties; or
   b) O; and 0 or 1 —CH$_2$— moieties and —CH=CH— or —C≡C—; and
2) Ar;
e.g., —O—Ar—, —Ar—CH$_2$—O—, —O—Ar—(CH$_2$)$_2$—, —OAr—CH=CH—, —O—Ar—C≡C—, —O—CH$_2$—Ar—, —O—CH$_2$—Ar—(CH$_2$)$_2$, —O—CH$_2$Ar—CH=CH—, —O—CH$_2$Ar—C≡C—, and the like; or in another embodiment A comprises:
1) a) S; and 0, 1, 2, or 3 —CH$_2$— moieties; or
   b) S; and 0 or 1 —CH$_2$— moieties and —CH=CH— or —C≡C—; and
2) Ar;
e.g., —S—Ar—, —Ar—CH$_2$—S—, —S—Ar—(CH$_2$)$_2$—, —SAr—CH=CH—, —S—Ar—C≡C—, —S—CH$_2$—Ar—, —S—CH$_2$—Ar—(CH$_2$)$_2$, —S—CH$_2$Ar—CH=CH—, —S—CH$_2$Ar—C≡C—, and the like.

In another embodiment, the sum of m and o is 2, 3, or 4 wherein one CH$_2$ may be replaced with S or O and 1 —CH$_2$—CH$_2$— may be replaced by —CH=CH— or —C≡C—.

In another embodiment, the sum of m and o is 3 wherein one CH$_2$ may be replaced with S or O and 1 —CH$_2$—CH$_2$— may be replaced by —CH=CH— or —C≡C—.

In another embodiment, the sum of m and o is 2 wherein one CH$_2$ may be replaced with S or O or 1 —CH$_2$—CH$_2$— may be replaced by —CH=CH— or —C≡C—.

In another embodiment, the sum of m and o is 4 wherein one CH$_2$ may be replaced with S or O and 1 —CH$_2$—CH$_2$— may be replaced by —CH=CH— or —C≡C—.

Interarylene refers to an aryl ring or ring system, including a heteroaryl ring or ring system, which connects two other parts of a molecule, i.e. the two parts are bonded to the ring in two distinct ring positions. Interarylene may be substituted or unsubstituted. Unsubstituted interarylene has no substituents other than the two parts of the molecule it connects. Substituted interarylene has substituents in addition to the two parts of the molecule it connects.

In one embodiment, Ar is substituted or unsubstituted interphenylene, interthienylene, interfurylene, interpyridinylene, interoxazolylene, and interthiazolylene. Substitutents of Ar must be stable, and each have from 0 to 4 carbon atoms, from 0 to 3 oxygen atoms, from 0 to 2 sulfur atoms, from 0 to 2 nitrogen atoms, from 0 to 3 fluorine atoms, from 0 to 1 chlorine atoms, from 0 to 1 bromine atoms, from 0 to 1 iodine atoms, and from 0 to 10 hydrogen atoms. If a substituent is acidic or basic, the number of atoms indicated above refers to the neutral form of the substituent. For example, neutral forms include —CO$_2$H, not —CO$_2^-$Na$^+$; or —NH$_3$, not —NH$_4^+$Cl$^-$.

In another embodiment A is —CH$_2$—Ar—OCH$_2$—. In another embodiment A is —CH$_2$-Ph-OCH$_2$—. In another embodiment, Ph (phenyl) is attached at the 1 and 3 positions, otherwise known as m-interphenylene, such as when A has the structure shown below.

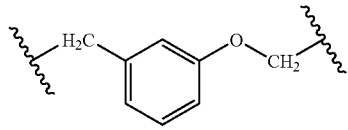

In another embodiment A is —(CH$_2$)$_6$—, cis —CH$_2$CH=CH—(CH$_2$)$_3$—, or —CH$_2$C≡C—(CH$_2$)$_3$—, wherein 1 or 2 carbon atoms may be replaced with S or O; or A is —(CH$_2$)$_2$-Ph- wherein one —CH$_2$— may be replaced with S or O.

In another embodiment A is —(CH$_2$)$_6$—, cis —CH$_2$CH=CH—(CH$_2$)$_3$—, or —CH$_2$C≡C—(CH$_2$)$_3$—, wherein 1 or 2 carbon atoms may be replaced with S or O; or A is —(CH$_2$)$_2$-Ph-.

In one embodiment, Ar is thienyl.

In other embodiments, A has one of the following structures.

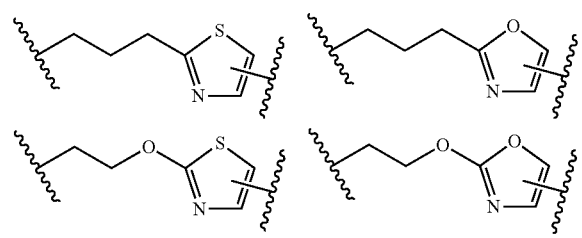

-continued

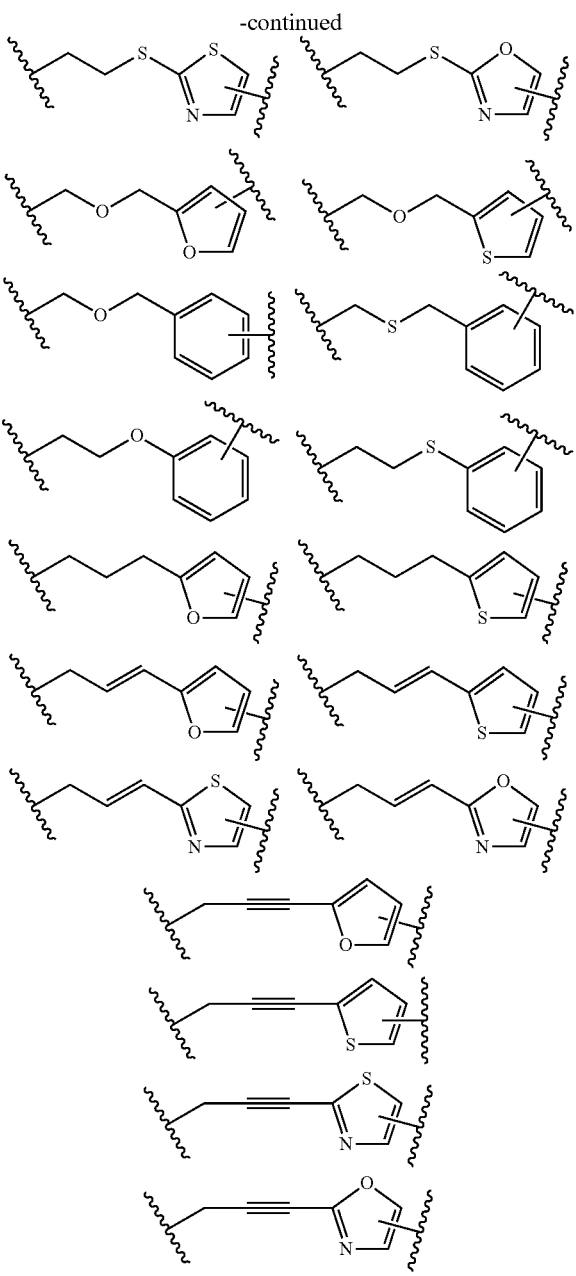

In another embodiment A is —CH$_2$OCH$_2$Ar—.
In another embodiment A is —CH$_2$SCH$_2$Ar—.
In another embodiment A is —(CH$_2$)$_3$Ar—.
In another embodiment A is —CH$_2$O(CH$_2$)$_4$—.
In another embodiment A is —CH$_2$S(CH$_2$)$_4$—.
In another embodiment A is —(CH$_2$)$_6$—.
In another embodiment A is cis —CH$_2$CH=CH—(CH$_2$)$_3$—.
In another embodiment A is —CH$_2$C≡C—(CH$_2$)$_3$—.
In another embodiment A is —S(CH$_2$)$_3$S(CH$_2$)$_2$—.
In another embodiment A is —(CH$_2$)$_4$OCH$_2$—.
In another embodiment A is cis —CH$_2$CH=CH—CH$_2$OCH$_2$—.
In another embodiment A is —CH$_2$CH≡CH—CH$_2$OCH$_2$—.
In another embodiment A is —(CH$_2$)$_2$S(CH$_2$)$_3$—.
In another embodiment A is —CH$_2$-Ph-OCH$_2$—, wherein Ph is interphenylene.

In another embodiment A is —CH$_2$-mPh-OCH$_2$—, wherein mPh is m-interphenylene.
In another embodiment A is —CH$_2$—O—(CH$_2$)$_4$—.
In another embodiment A is —CH$_2$—O—CH$_2$—Ar—, wherein Ar is 2,5-interthienylene.
In another embodiment A is —CH$_2$—O—CH$_2$—Ar—, wherein Ar is 2,5-interfurylene.
In another embodiment A is (3-methylphenoxy)methyl.
In another embodiment A is (4-but-2-ynyloxy)methyl.
In another embodiment A is 2-(2-ethylthio)thiazol-4-yl.
In another embodiment A is 2-(3-propyl)thiazol-5-yl.
In another embodiment A is 3-(methoxymethyl)phenyl.
In another embodiment A is 3-(3-propylphenyl).
In another embodiment A is 3-methylphenethyl.
In another embodiment A is 4-(2-ethyl)phenyl.
In another embodiment A is 4-phenethyl.
In another embodiment A is 4-methoxybutyl.
In another embodiment A is 5-(methoxymethyl)furan-2-yl.
In another embodiment A is 5-(methoxymethyl)thiophen-2-yl.
In another embodiment A is 5-(3-propyl)furan-2-yl.
In another embodiment A is 5-(3-propyl)thiophen-2-yl.
In another embodiment A is 6-hexyl.
In another embodiment A is (Z)-6-hex-4-enyl.

G is —H, —OH, —O-alkyl having from 1 to 6 carbon atoms, halo, C$_{1-6}$ alkyl, —CF$_3$, —CN, or =O.
In one embodiment, G is —H.
In another embodiment, G is —OH.
In another embodiment, G is —O-alkyl having from 1 to 6 carbon atoms. In other words, G is -OMe, -OEt, -OiPr, etc., up to 6 carbon atoms.
In another embodiment, G is halo.
In another embodiment, G is C$_{1-6}$ alkyl.
In another embodiment, G is —CF$_3$.
In another embodiment, G is —CN.
In another embodiment, G is or =O.

G' is —H, —OH, —O-alkyl having from 1 to 6 carbon atoms, halo, C$_{1-6}$ alkyl, —CF$_3$, —CN, or =O.
In one embodiment, G' is —H.
In another embodiment, G' is —OH
In another embodiment, G' is —O-alkyl having from 1 to 6 carbon atoms. In other words, G' is —OMe, —OEt, —OiPr, etc., up to 6 carbon atoms.
In another embodiment, G' is halo.
In another embodiment, G' is C$_{1-6}$ alkyl.
In another embodiment, G' is —CF$_3$.
In another embodiment, G' is —CN.
In another embodiment, G' is or =O.

G and G' are independent, meaning that the identity of one does not affect the identity of the other. Thus, they could be the same, for example, G and G' could be —H. Or they could be different, for example, G might be —H and G' might be =O.

B is aryl.
Aryl is an aromatic ring or ring system such as phenyl, naphthyl, biphenyl, and the like. Aryl also includes heteroaryl, which is an aromatic ring or ring system containing one or more O, N, or S heteroatoms. Aryl may be substituted or unsubstituted, and unless otherwise indicated, "aryl" or "heteroaryl" should be taken to mean "substituted or unsubstituted aryl" or "substituted or unsubstituted heteroaryl." Similarly, unless otherwise indicated, any specific aryl ring such as "phenyl," "pyridinyl," "thienyl," "furyl," etc., should be taken to mean "substituted or unsubstituted phenyl," "substituted or unsubstituted pyridinyl," "substituted or unsubstituted thienyl," "substituted or unsubstituted furyl," etc. The substituents of aryl for B must be stable, and may have from 0 to 12 carbon atoms, from 0 to 4 oxygen atoms, from 0 to 2 sulfur atoms, from 0 to 3 nitrogen atoms, from 0 to 3 fluorine atoms, from 0 to 2 chlorine atoms, from 0 to 2 bromine atoms, and from 0 to 1 iodine atoms. If a substituent is acidic or basic, the number of atoms indicated above refers to the neutral form of the substituent. For example, neutral forms include —$CO_2H$, not —$CO_2^-Na^+$; or —$NH_3$, not —$NH_4^+Cl^-$.

In one embodiment, B is phenyl.

In another embodiment, B is pyridinyl.

In another embodiment, B is thienyl.

In another embodiment, B is furyl.

Examples of substituents may include the following, subject to the constraints defined herein for that particular moiety or substituent:

A. Hydrocarbyl, including, but not limited to:
  a. alkyl, such as:
    linear alkyl, e.g. methyl, ethyl, n-propyl, n-butyl, n-pentyl, n-hexyl, etc.,
    branched alkyl, e.g. iso-propyl, t-butyl and other branched butyl isomers, branched pentyl isomers, etc.,
    cycloalkyl, e.g. cyclopropyl, cyclobutyl, cyclopentyl, cyclohexyl, etc.,
    combinations of linear, branched, and/or cycloalkyl;
  b. alkenyl, which is hydrocarbyl having 1 or more double bonds, including linear, branched, or cycloalkenyl
  c. alkynyl, which is hydrocarbyl having 1 or more triple bonds, including linear, branched, or cycloalkynyl;
  d. combinations of alkyl, alkenyl, and/or akynyl B. alkyl-CN, such as —$CH_2$—CN, —$(CH_2)_2$—CN; —$(CH_2)_3$—CN, and the like;

C. Hydroxy, —OH

D. hydroxyalkyl, i.e. alkyl-OH, such as hydroxymethyl, hydroxyethyl, and the like;

E. ether substituents, including —O-alkyl, alkyl-O-alkyl, and the like;

F. thioether substituents, including —S-alkyl, alkyl-S-alkyl, and the like;

G. amine substituents, including —$NH_2$, —NH-alkyl, —N-alkyl$^1$alkyl$^2$ (i.e., alkyl$^1$ and alkyl$^2$ are the same or different, and both are attached to N), alkyl-$NH_2$, alkyl-NH-alkyl, alkyl-N-alkyl$^1$alkyl$^2$, and the like;

H. aminoalkyl, meaning alkyl-amine, such as aminomethyl (—$CH_2$-amine), aminoethyl, and the like;

I. ester substituents, including —$CO_2$-alkyl, —$CO_2$-phenyl, etc.;

J. other carbonyl substituents, including aldehydes; ketones, such as acyl, including, acetyl, propionyl, and benzoyl substituents;

K. fluorocarbons or hydrofluorocarbons such as —$CF_3$, $CH_2CF_3$, etc.; and

L. other nitrogen containing substituents such as —CN and —$NO_2$,

M. other sulfur containing substitutents such as sulfide, sulfonyl or sulfoxide;

N. aryl;

O. combinations of the above are also possible, subject to the constraints defined;

P. Alternatively, a substituent may be —F, —Cl, —Br, or —I.

In one embodiment Y is $CO_2R^4$.

In another embodiment G is hydrogen.

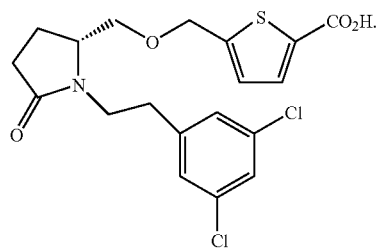

Another embodiment is a compound having a formula:

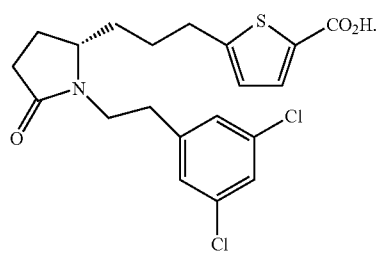

Another embodiment is a compound having a formula:

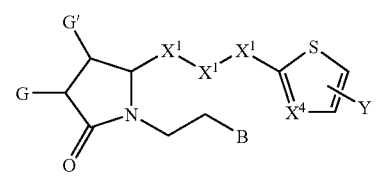

wherein each $X^1$ is independently —$CH_2$—, —O—, or —S—; and
$X^4$ is —CH— or —N—.

Thus, since each $X^1$ is independent, $X^1$—$X^1$—$X^1$ could be —$(CH_2)_3$—, —$O(CH_2)_2$—, —$S(CH_2)_2$—, —$(CH_2)_2O$—, —$(CH_2)_2S$—, —$CH_2OCH_2$—, —$CH_2SCH_2$—, and the like.

In one embodiment $X_4$ is —CH—.

In another embodiment $X_4$ is —N—.

Another embodiment is a compound having a formula:

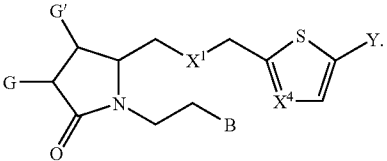

Another embodiment is a compound having a formula:

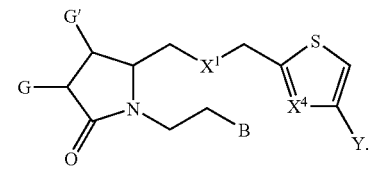

In another embodiment G is hydrogen.

In another embodiment G' is —H, —OH, —OCH₃, F, Cl, —CH₃, —CF₃, —CN, or =O.

In another embodiment G' is —H.

In another embodiment G is —H, —OH, —OCH₃, F, Cl, —CH₃, —CF₃, —CN, or =O.

In another embodiment B is phenyl or pyridinyl.

In another embodiment B is phenyl.

In another embodiment B is phenyl with from 1 to 3 substituents independently selected from: —F, —Cl, —Br, —I, —OH, —NH₂, —NO₂, —OCH₃, —C$_{1-4}$ alkyl, —CF₃, —CN, —CHO, —CO₂H, and —CH₂OH.

In another embodiment B is dichlorophenyl.

Another embodiment is use of a compound disclosed herein in the manufacture of a medicament for the treatment of glaucoma or ocular hypertension in a mammal.

Another embodiment is a method of treating glaucoma or ocular hypertension comprising administering a compound disclosed herein to a mammal in need thereof.

A liquid composition comprising a compound disclosed herein and a pharmaceutically acceptable excipient.

The structures depicted below are hypothetical examples of useful compounds.

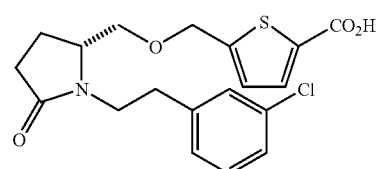

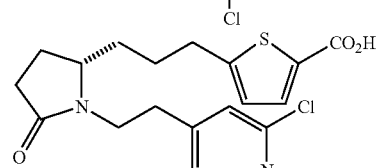

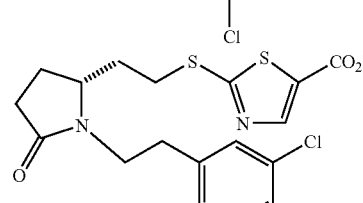

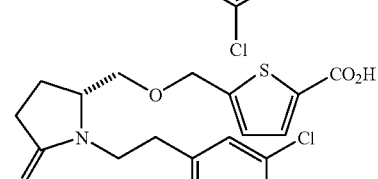

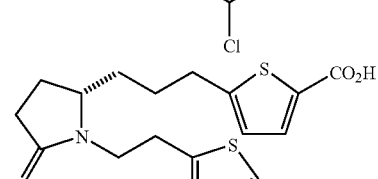

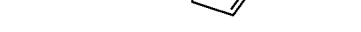

-continued

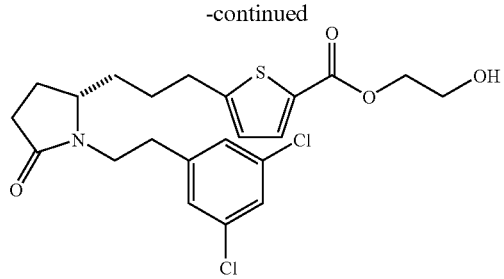

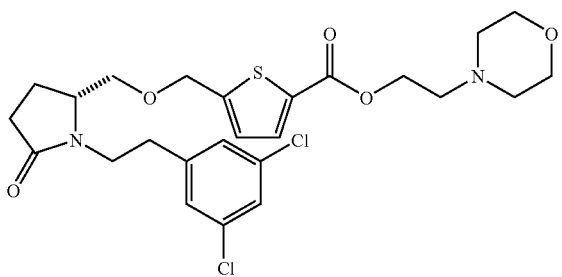

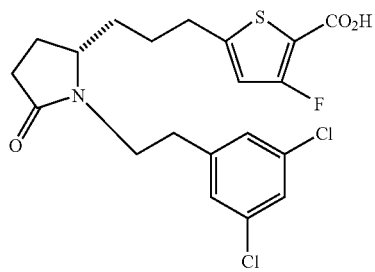

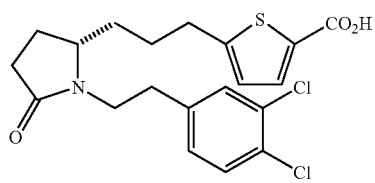

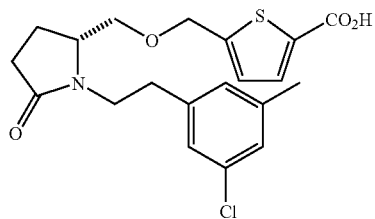

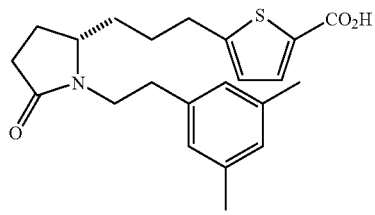

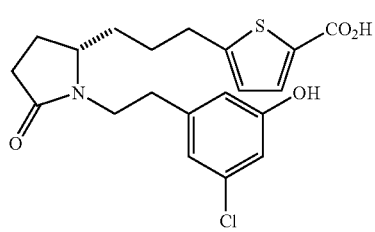

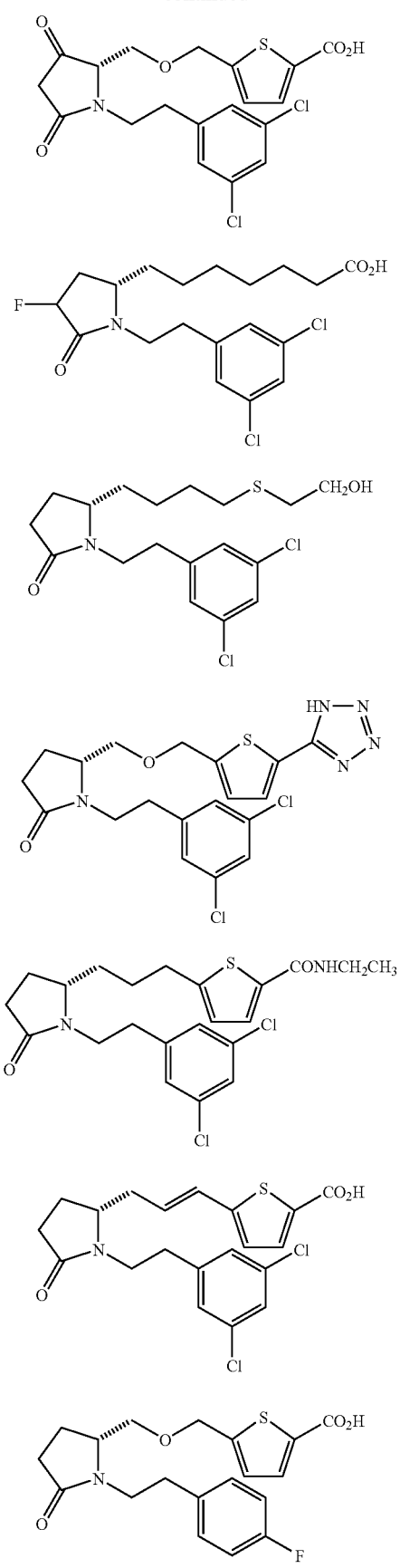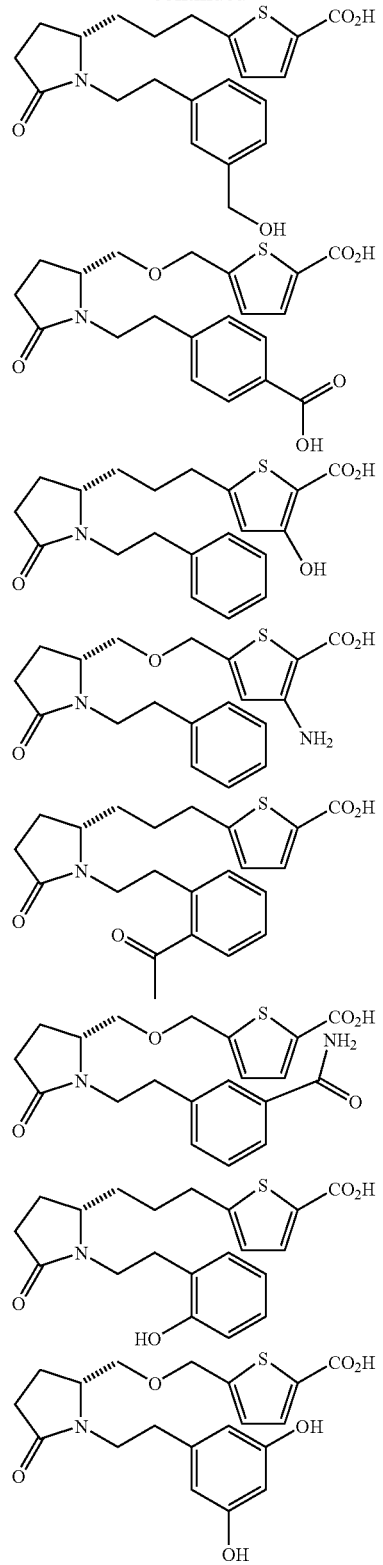
Synthetic Methods
The compounds disclosed herein can be prepared by methods known in the art. For example, Schemes A-C illustrate an exemplary general method that might be employed.

Scheme A

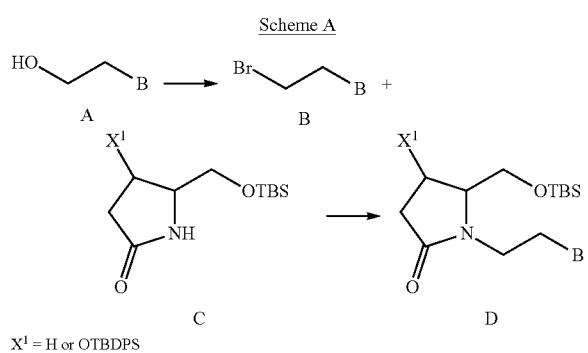

$X^1$ = H or OTBDPS

The ω-chain (—CH$_2$CH$_2$—B) may be attached to the pyrrolidin-2-one core by employing a method such as that shown in Scheme A. The coupling between B and C to obtain the coupled compound D could be carried out by a number of methods known in the art. For example, the reaction might be catalyzed using a base such as sodium hydride. A different leaving group than Br might also be used for compound B.

Scheme B

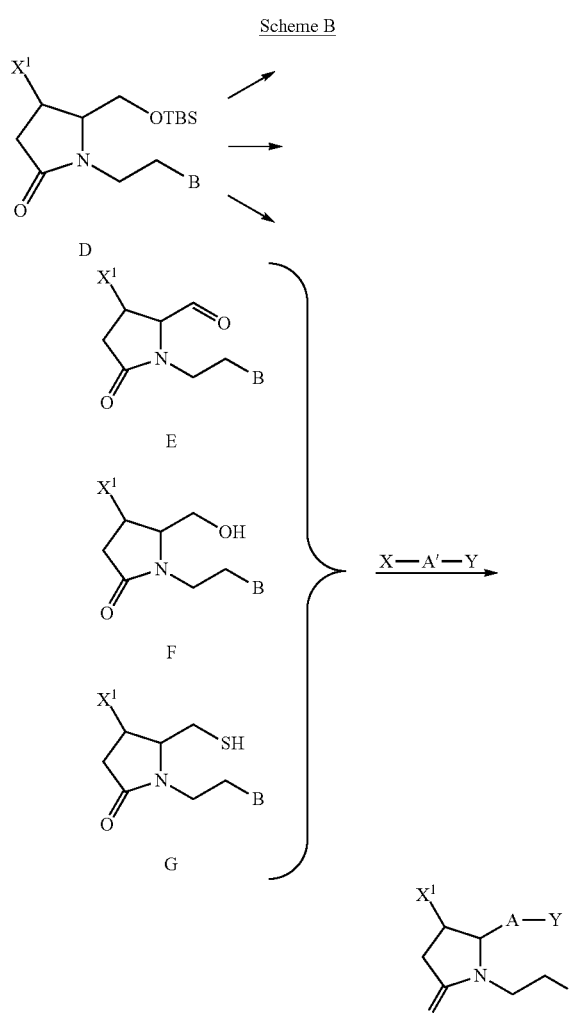

The protected alcohol of compound D provides a good handle to prepare a wide range of α-chains. For example, it could be oxidized to an aldehyde (E) and coupled to X-A'-Y via a Wittig-type coupling, where X is a phosphonium species. This may be hydrogenated to give a saturated C—C bond, or the unsaturated bond may be retained. Compound D could also be deprotected (F) or converted to SH (G) and coupled to X-A'-Y via a nucleophilic substitution, where X is a leaving group.

Scheme C

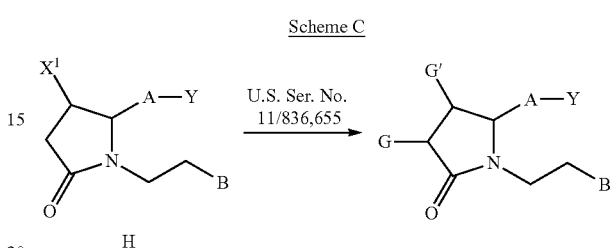

Substituents on the pyrrolidin-2-one core may be added by employing methods described in U.S. patent application Ser. No. 11/836,655, filed Aug. 9, 2007, on Compound H.

Scheme 1

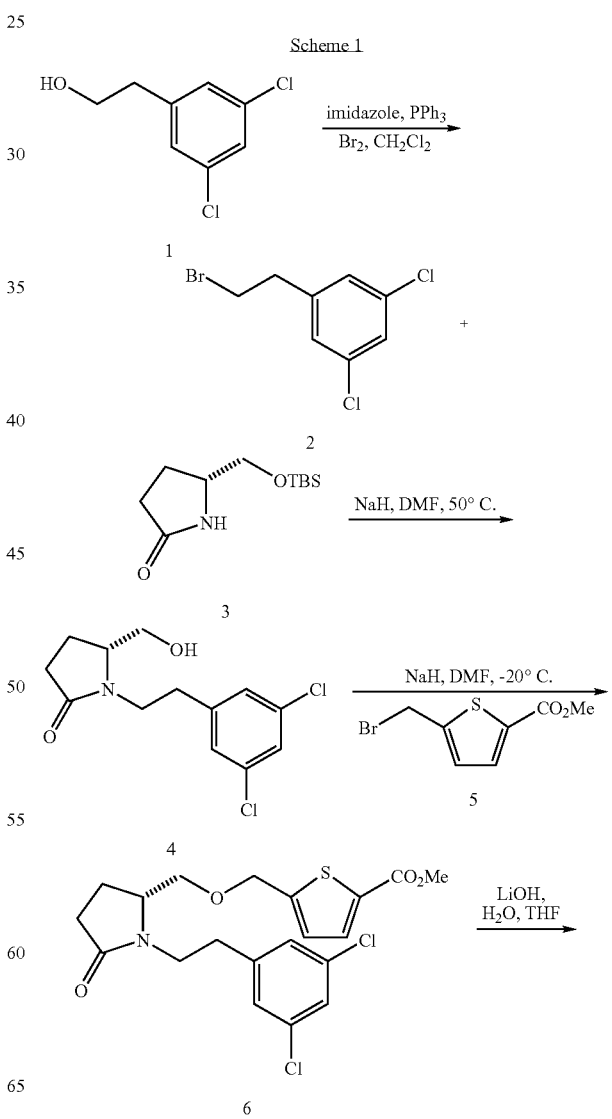

-continued

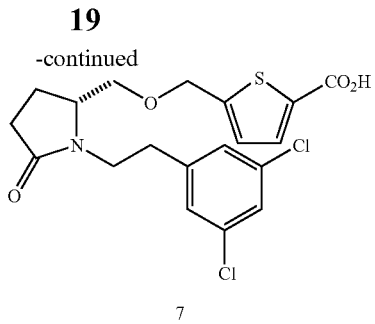

7

EXAMPLE 1

(R)-5-(((1-(3,5-dichlorophenethyl)-5-oxopyrrolidin-2-yl)methoxy)methyl)thiophene-2-carboxylic acid (7)

Step 1. Preparation of Bromide 2

Bromine (0.80 mL, 15.5 mmol) was added to a solution of triphenylphosphine (4.12 g, 15.7 mmol) and imidazole (1.07 g, 15.7 mmol) in $CH_2Cl_2$ (52 mL) at 0° C. and the mixture was allowed to warm to room temperature. A solution of 2-(3,5-dichlorophenyl)ethanol (1, 2.5 g, 13.1 mmol) in $CH_2Cl_2$ (13 mL) was added via cannula. After 30 min at room temperature, the mixture was filtered through celite, washing with excess $CH_2Cl_2$. The filtrate was concentrated in vacuo. The crude residue was purified by chromatography on 120 g silica (hexanes →20% EtOAc/hexanes, gradient) to afford 3.13 g (94%) of bromide 2.

Step 2. Alkylation of 3 with 2 to Give 4

Sodium hydride (80 mg of a 60% dispersion in oil, 2.0 mmol) was added to a solution of 3 (115 mg, 0.50 mmol) in DMF (4 mL). After 45 min at room temperature, a solution of bromide 2 (255 mg, 1.0 mmol) in DMF (1 mL) was added via cannula. The mixture was heated at 50° C. for 18 h, then cooled to room temperature and quenched with saturated aqueous $NH_4Cl$ (20 mL). The mixture was extracted with EtOAc (125 mL). The organic phase was washed with water (2×50 mL) and brine (50 mL), then dried ($Na_2SO_4$), filtered and concentrated in vacuo. The crude residue was purified by chromatography on 12 g silica gel (hexanes →EtOAc, gradient) to afford 39 mg (27%) of alcohol 4.

Step 3. Alkylation of 4 with 5 to Give 6

Sodium hydride (21 mg of a 60% dispersion in oil, 0.53 mmol) was added to a solution of 4 (100 mg, 0.35 mmol) in DMF (0.43 mL) at 0° C. and the mixture was allowed to warm to room temperature. After 30 min at room temperature, the mixture was cooled to −40° C. and a solution of bromide 5 (see U.S. Provisional Patent Application 60/804,680, filed Jun. 14, 2006, 70 mg, 0.30 mmol) in DMF (0.43 mL) was added via cannula. After 10 min at −40° C., the reaction was partitioned between water (10 mL) and $CH_2Cl_2$ (20 mL). The phases were separated and the aqueous phase was extracted with additional $CH_2Cl_2$ (2×10 mL). The combined organic phase was dried ($MgSO_4$), filtered and concentrated in vacuo. The crude residue was purified by chromatography on silica gel (hexanes →EtOAc, gradient) to afford 84 mg (64%) of 6.

Step 4. Saponification of 6 to Give 7

Aqueous 1.0 N lithium hydroxide (0.36 mL, 0.36 mmol) was added to a solution of ester 6 (40 mg, 0.090 mmol) in THF (0.9 mL). The solution was heated at 40° C. for 18 h, then cooled to room temperature. The mixture was quenched with 10% aqueous HCl (10 mL) and extracted with EtOAc (2×20 mL). The combined organic phase was washed with brine (10 mL), dried ($MgSO_4$), filtered and concentrated in vacuo. Purification of the crude residue by chromatography on 4 g silica gel ($CH_2Cl_2$→10% MeOH/$CH_2Cl_2$, gradient) afforded 11 mg (28%) of the title compound.

Scheme 2

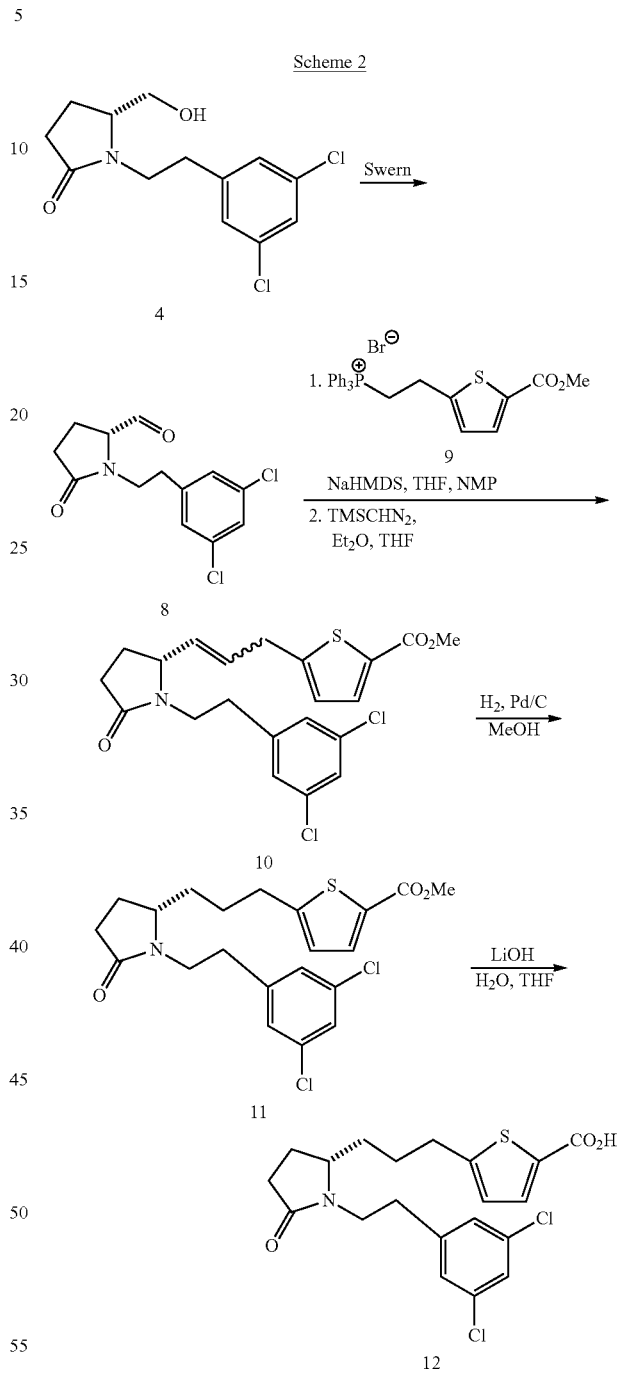

EXAMPLE 2

(S)-5-(3-(1-(3,5-dichlorophenethyl)-5-oxopyrrolidin-2-yl)propyl)thiophene-2-carboxylic acid (12)

Step 1. Oxidation of 4 to Give 8

DMSO (65 μL, 0.92 mmol) was added to a solution of oxalyl chloride (220 μL of a 2.0 M solution in $CH_2Cl_2$, 0.44 mmol) and $CH_2Cl_2$ (3.1 mL) at −78° C. After 15 min, a solution of alcohol 4 (100 mg, 0.35 mmol) in CH$_2$Cl$_2$ (1.0 mL) was added via cannula. After 15 min, triethylamine (412 µL, 2.96 mmol) was added and the reaction mixture was allowed to warm to room temperature. After 1 h at room temperature the mixture was partitioned between CH$_2$Cl$_2$ (25 mL) and saturated aqueous NaHCO$_3$ (25 mL). The phases were separated and the aqueous phase was extracted with CH$_2$Cl$_2$ (2×30 mL). The combined organic phase was dried (Na$_2$SO$_4$), filtered and concentrated in vacuo to afford 100 mg (quant.) of crude aldehyde 8 which was used without further purification.

Step 2. Wittig Reaction of 8 with 9, Followed by Esterification to Give 10

A solution of sodium bis(trimethylsilyl)amide (0.7 mL of a 1.0 M solution in THF, 0.70 mmol) was added to a solution of phosphonium salt 9 (see U.S. Prov PA No. 60/894,267, 173 mg, 0.35 mmol) in 1-methyl-2-pyrrolidinone (NMP, 0.5 mL) at 0° C. After stirring vigorously for 30 min at 0° C., the mixture was cooled to −20° C. and a solution of aldehyde 8 (50 mg, 0.17 mmol) in THF (0.4 mL) was added by syringe. After 30 min at −20° C. the mixture was allowed to warm to 0° C. After 1 h at 0° C., the reaction was quenched with saturated aqueous NH$_4$Cl (10 mL) and diluted with CH$_2$Cl$_2$ (25 mL). The resulting emulsion was filtered through celite, washing with CH$_2$Cl$_2$. The phases were separated and the aqueous phase was extracted with CH$_2$Cl$_2$ (3×75 mL). The combined organic phase was dried (Na$_2$SO$_4$), filtered and concentrated in vacuo. The crude material was dissolved in THF (0.87 mL) and treated dropwise with a solution of (trimethylsilyl)diazomethane (0.43 mL of a 2.0 M solution in Et$_2$O, 0.86 mmol). After 30 min at room temperature, the reaction mixture was concentrated in vacuo.

Purification of the crude residue by chromatography on 12 g silica gel (CH$_2$Cl$_2$→15% MeOH/CH$_2$Cl$_2$, gradient) gave a poor separation of desired product and impurities. Fractions containing the desired product were concentrated in vacuo and purified by chromatography on 12 g silica gel (50% EtOAc/hexanes→EtOAc, gradient) to afford 14 mg (18%) of ester 10 as a mixture of olefin isomers.

Step 3. Hydrogenation of 10 to Give 11

Palladium on carbon (10 wt. %, 6.8 mg) was added to a solution of alkene 10 (14 mg, 0.032 mmol) in MeOH (0.7 mL). A hydrogen atmosphere was established by evacuating and refilling with hydrogen (5×) and the mixture was stirred under a balloon of hydrogen. After 18 h, the reaction was filtered through celite, washing with excess MeOH. The filtrate was concentrated in vacuo. Purification of the crude residue on 4 g silica gel (35% EtOAc/hexanes→80% EtOAc/hexanes, gradient) afforded 3 mg (21%) of 11.

Step 4. Saponification of 11 to Give 12

Aqueous 1.0 N lithium hydroxide (0.05 mL, 0.05 mmol) was added to a solution of ester 11 (2 mg, 0.0045 mmol) in THF (0.1 mL). After 18 h at 30° C., the mixture was cooled and the volatiles were removed under as stream of nitrogen. The residue was diluted with water (0.2 mL) and acidified with 1 N aqueous HCl (0.5 mL). The mixture was extracted with EtOAc (3×2 mL). The combined extracts were washed with brine (1 mL), dried (Na$_2$SO$_4$), filtered and concentrated in vacuo. Purification of the crude residue by chromatography on 4 g silica gel (CH$_2$Cl$_2$→20% MeOH/CH$_2$Cl$_2$, gradient) afforded 1.3 mg (67%) of the title compound.

In vitro Testing

U.S. patent application Ser. No. 11/553,143, filed on Oct. 26, 2006, incorporated by reference herein, describes the methods used to obtain the in vitro data in the table below.

TABLE 1

| Structure | EP2 data | | | EP4 data | | Other Receptors (EC50 in nM) | | | | | |
| --- | --- | --- | --- | --- | --- | --- | --- | --- | --- | --- | --- |
| | flipr | cAMP | | flipr | | | | | | | |
| | EC50 | EC50 | KI | EC50 | KI | hFP | hEP1 | hEP3A | hTP | hIP | hDP |
| 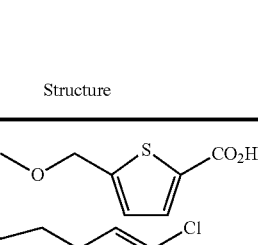 | >10000 | 4 | 159 | >10000 | 7990 | NA | NA | NA | NA | NA | NA |
| 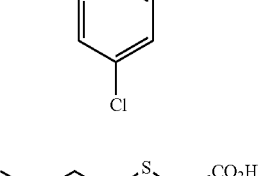 | 8412 | 2.2 | 24 | NT | >10000 | NA | NA | NA | NA | NA | 6225 |

What is claimed is:

1. A compound of the formula:

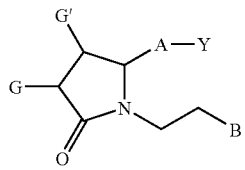

wherein Y has from 0 to 14 carbon atoms and is: a carboxylic acid group, or an amide or ester thereof; hydroxymethyl or an ether thereof; or a tetrazolyl functional group;

A is —$(CH_2)_6$—, cis —$CH_2CH$=$CH$—$(CH_2)_3$—, or —$CH_2C$≡$C$—$(CH_2)_3$—, wherein 1 or 2 carbon atoms may be replaced by S or O; or A is —$(CH_2)_m$—Ar—$(CH_2)_o$— wherein Ar is interarylene, the sum of m and o is 1, 2, 3, or 4, and wherein 1 —$CH_2$— may be replaced by S or O, and 1 —$CH_2$—$CH_2$— may be replaced by —CH=CH— or —C≡C—;

G and G' are independently —H, —OH, —O-alkyl having from 1 to 6 carbon atoms, halo, $C_{1-6}$ alkyl, —$CF_3$, —CN, or =O; and B is aryl.

2. The compound of claim 1 wherein Y is —$CO_2R^4$, —$CONR^5R^6$, —$CON(CH_2CH_2OH)_2$, —$CONH(CH_2CH_2OH)$, —$CH_2OH$,

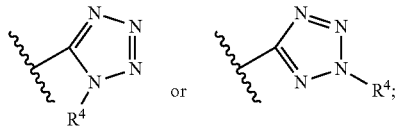

wherein $R^4$, $R^5$ and $R^6$ are independently H, $C_1$-$C_6$ alkyl, $C_{1-6}$ hydroxyalkyl, unsubstituted phenyl, or unsubstituted biphenyl.

3. The compound of claim 2 wherein Y is $CO_2R^4$.

4. The compound of claim 3 wherein G is hydrogen.

5. The compound of claim 4 of the formula:

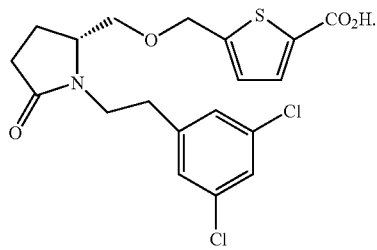

6. The compound of claim 4 of the formula:

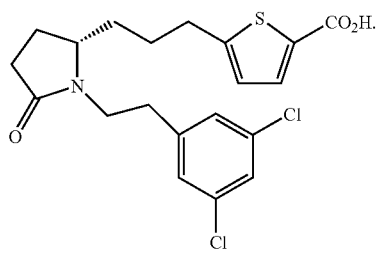

7. The compound of claim 1 of the formula:

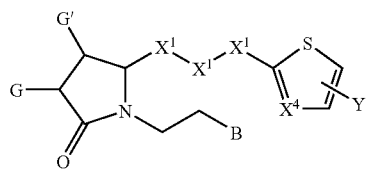

wherein each $X^1$ is independently —$CH_2$—, —O—, or —S—; and $X^4$ is —CH— or —N—.

8. The compound of claim 7 of the formula

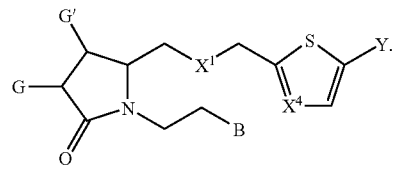

9. The compound of claim 7 of the formula

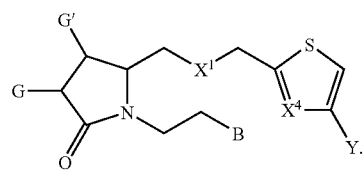

10. The compound of claim 1 wherein G is hydrogen.

11. The compound of claim 1 wherein G' is —H, —OH, —$OCH_3$, F, Cl, —$CH_3$, —$CF_3$, —CN, or =O.

12. The compound of claim 11 wherein G' is —H.

13. The compound of claim 11 wherein G is —H, —OH, —$OCH_3$, F, Cl, —$CH_3$, —$CF_3$, —CN, or =O.

14. The compound of claim 1 wherein B is phenyl or pyridinyl.

15. The compound of claim 14 wherein B is phenyl.

16. The compound of claim 15 wherein B is phenyl with from 1 to 3 substituents independently selected from: —F, —Cl, —Br, —I, —OH, —$NH_2$, —$NO_2$, —$OCH_3$, —$C_{1-4}$ alkyl, —$CF_3$, —CN, —CHO, —$CO_2H$, and —$CH_2OH$.

17. The compound of claim 14 wherein B is dichlorophenyl.

18. A method of treatment for glaucoma or ocular hypertension comprising administering a compound according to claim 1 to a mammal in need thereof, wherein treatment is mitigation.

19. A liquid composition comprising a compound according to claim 1 and a pharmaceutically acceptable excipient.

* * * * *